United States Patent [19]

Misra et al.

[11] Patent Number: 5,075,472

[45] Date of Patent: Dec. 24, 1991

[54] ALUMINUM HYDROXIDE LITHIUM OXALATE COMPOUNDS

[75] Inventors: Chanakya Misra, Pittsburgh; Anthony J. Perrotta, Monroeville, both of Pa.

[73] Assignee: Aluminum Company of America, Pittsburgh, Pa.

[21] Appl. No.: 589,536

[22] Filed: Sep. 28, 1990

[51] Int. Cl.$^5$ ............................................... C07F 5/06
[52] U.S. Cl. ..................................................... 556/179
[58] Field of Search ........................................ 556/179

[56] References Cited

U.S. PATENT DOCUMENTS 4,183,843  1/1980  Koenig et al. ..................... 260/40
4,565,716  1/1986  Williams, Jr. et al. ............. 427/216

Primary Examiner—Jose G. Dees
Assistant Examiner—Porfirio Nazario
Attorney, Agent, or Firm—Andrew Alexander

[57] ABSTRACT

Disclosed is a crystalline compound and a method of making the compound. The composition is expressed in terms of molar ratios by the formula $[Al_2(OH)_6] \cdot X \cdot [Li_2C_2O_4]$ where X is in the range of 0.1 to 1. The method comprises the steps of adding $Al(OH)_3$ to an aqueous solution containing lithium oxalate to provide a mixture; and reacting said mixture to form said new compositions.

16 Claims, 2 Drawing Sheets

ALUMINUM HYDROXIDE LITHIUM OXALATE COMPOUNDS

This invention relates to a new product containing aluminum hydroxide, and more particularly, it relates to new crystalline compounds formed with aluminum hydroxides and oxalate material and the method of making the compounds.

The present invention provides a method for combining an oxalate, e.g., lithium oxalate, with aluminum hydroxide to produce novel compounds. In addition, the novel compounds may be further treated to produce novel alumina materials.

SUMMARY OF THE INVENTION

It is, therefore, an object of the present invention to provide a method for making novel compounds comprised of aluminum hydroxide and lithium oxalate.

It is a further object to provide a method of making novel compounds of aluminum hydroxide, e.g., aluminum trihydrate ($Al_2O_3 \cdot 3H_2O$) and lithium oxalate.

Yet it is another object of this invention to provide novel compounds of aluminum hydroxide and lithium oxalate.

It is another object of the present invention to provide a method for producing new products of aluminum hydroxide and lithium oxalate having a morphology different from the starting aluminum hydroxide.

SUMMARY OF THE INVENTION

In accordance with these objects, there is provided a crystalline compound and a method of making the compound. The composition is expressed in terms of molar ratios by the formula $[Al_2(OH)_6] \cdot X[Li_2C_2O_4]$ where X is in the range of 0.1 to 1. The method comprises the steps of adding $Al(OH)_3$ to an aqueous solution containing lithium oxalate to provide a mixture; and reacting said mixture to form the new compositions.

DETAILED DESCRIPTION OF THE PREFERRED EMBODIMENTS

Figure 1:
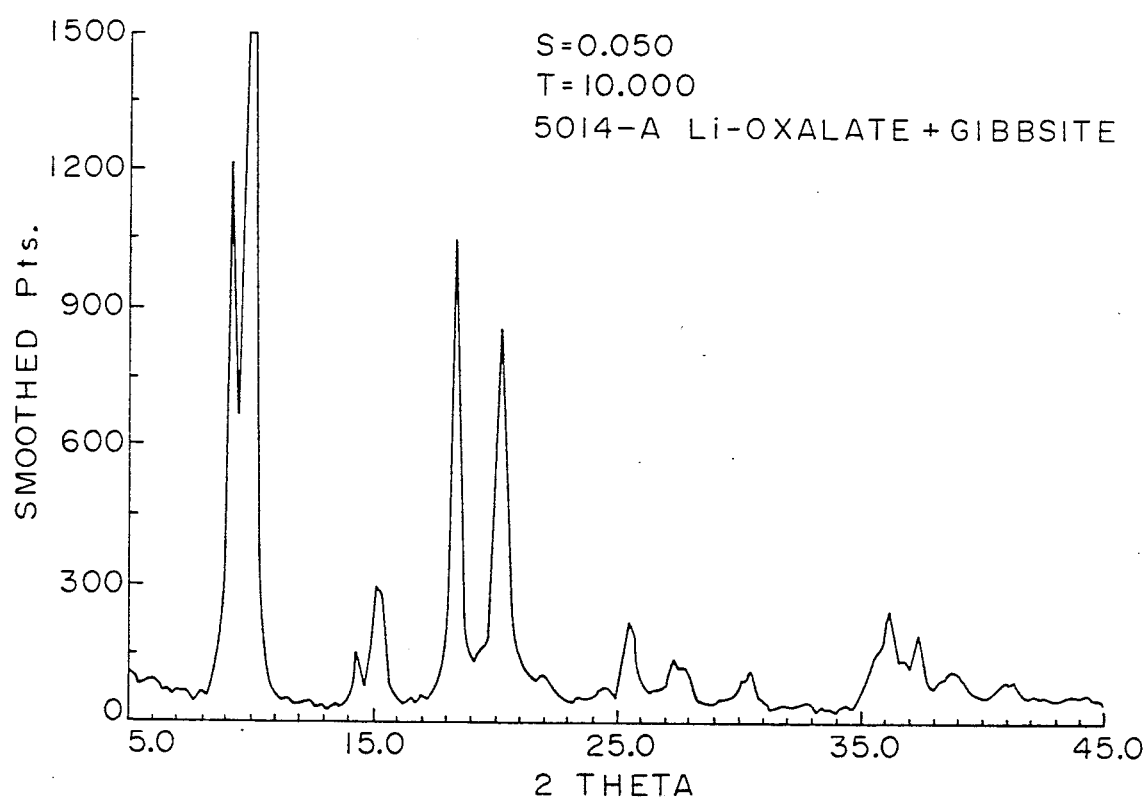
FIG. 1 shows X-ray diffraction lines characteristic of a new compound resulting from gibbsite and lithium oxalate.

The subject invention provides novel compounds comprised of aluminum hydroxide, e.g., gibbsite, bayerite, boehmite, nordstrandite, etc., and lithium oxalate. The use of aluminum hydroxide herein is meant to include $Al_2O_3 \cdot 3H_2O$ and $Al(OH)_3$ which are sometimes referred to as alumina trihydrate, hydrated alumina, hydrated aluminum oxide or aluminum trihydroxide. Further, aluminum hydroxide as used herein is intended to define a broad spectrum of hydroxides ranging from those which may contain few hydroxides, e.g., activated or partially calcined forms of aluminum oxide (alumina) to more hydrated forms which may comprise mainly hydroxide, e.g., $Al(OH)_{n=1 \text{ to } 3}$. It has been found, however, that the metal hydroxide form, rather than the metal oxide form, provides a more desirable product with which the lithium oxalate can react. However, for certain applications, dehydrated or activated forms of the aluminum hydroxide may be preferred due to the higher surface area of such particles.

The invention is primarily directed to the use of aluminum hydroxide particles as materials for reaction with the lithium oxalate to form the new material. The lithium oxalate can react with hydroxyl units of aluminum hydroxide substrates to change the characteristics of the product.

With respect to the aluminum hydroxides used in the present invention, it is preferred that they are provided in particulate form for certain applications. Particle sizes can range from as low as 50 Å to provide large external surfaces and up to 250 μm to produce large particle size products. Typically, the particle size is 0.1 to 100 microns. It will be appreciated that uses, for example, flocculation, flame retardance in polymers, heterogeneous catalysts and adsorbents, can require different particle sizes. However, normally the particle size is greater than 0.1 micron. Typical particle size distributions, when the particles comprise aluminum hydroxide, are 0.1-1, 3-6, 7-12, 10-18, 18-32, 32-63 and 50-200 microns.

With respect to particle morphology of the aluminum hydroxides used in the invention, both crystalline and gel type, including pseudoboehmite aluminum hydroxides, can be used. With respect to purity, the level of impurity should be minimized depending on the end use. For adsorbents, for example, the metal hydroxide should have a purity level of over 80%, preferably 95% or greater. Surface area of the particle is preferred t be high with typical surface areas, for example, being in the range of 0 10 to 600 $m^2/g$.

To produce the novel material comprising the aluminum hydroxide reacted with lithium oxalate, the reaction is carried out in an aqueous containing media, e.g., water containing organic solvent. However, prior to the reaction, the lithium oxalate may be first dissolved in an aqueous solvent or medium such as water or an alcohol or a water-alcohol combination. Alcohols which may be used include methanol, ethanol, propanol and butanol or the like. Butanol and higher carbon, e.g., 5 or 6 carbon, alcohols may be used at higher than room temperature. Preferably, 0.05 to 2.0 moles of lithium oxalate is used for each mole of aluminum hydroxide.

Aluminum hydroxide, as noted earlier, is added in an amount which permits a controlled molar ratio of aluminum hydroxide to lithium oxalate, e.g., 0.1 to 2.0 moles of lithium oxalate per mole of aluminum hydroxide. After addition of aluminum hydroxide to the solvent to provide a mixture thereof, the temperature may be raised above room temperature, e.g., 150° C., to permit reaction between aluminum hydroxide and lithium oxalate to take place. Thus, the temperature can range from 25° C. to 300° C. or 400° C., with temperatures of 100° to 250° C. having been found to be quite suitable. The time at temperature should be sufficient for the reaction to take place and may be as short as a few minutes or extend for several hours or longer with typical times being about 1 to 10 hours. For example, 2 to 4 hours have been found to be adequate digesting for lithium oxalate to react with aluminum hydroxide such as Bayer alumina hydrate. Further, these times and temperatures are also dependent on the concentration of the lithium oxalate.

For purposes of heating a mixture of the aluminum hydrate and lithium oxalate solution, it has been found that a closed vessel is beneficial. The closed vessel permits pressure to build autogenously.

The reaction is carried out at higher than atmospheric pressure, preferably from about 2 psi to 250 psi above atmosphere and typically about 5 to 200 psi above atmospheric pressure. The closed vessel is beneficial by controlling solvent loss.

After the aluminum hydroxide and lithium oxalate have been digested or reacted, the new product can be separated from the solvent media by filtering, for example. Thereafter, it may be washed and dried at temperatures below about 300° C.

The reaction is not limited to lithium oxalate but may be applied to other lithium salts of dicarboxylic acid such as lithium succinate, for example.

While the inventor does not wish to be bound by any particular theory of reaction, it is believed that when an aluminum hydroxide particle, for example, gibbsite, is brought into contact with lithium oxalate, a reaction or intercalation, or a combination thereof, of the lithium oxalate on the aluminum hydroxide takes place.

It is believed that in one aspect of the reaction, intercalation of the lithium oxalate in the hydroxide layers of the aluminum hydroxide are obtained, that is, not just surface hydroxides react. Thus, a novel compound is formed as a result of this reaction. This is shown by the X-ray diffraction pattern obtained for the compound. That is, even though the pattern of the new compound has lines corresponding to that of the Al(OH)$_3$, additional new X-ray diffraction lines characteristic of the new compound are observed or are present, as will be seen in FIG. 1, for example. This evidences both the old structure of the Al(OH)$_3$ and the new structure of the novel compound. The new compound may be defined by the formula, expressed in terms of molar ratios:

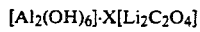

where X can be 1 or less than 1, e.g., about 0.1 to 1.

Thus, it can be seen that hydroxyl groups in gibbsite, as well as those on the surface, can be reacted with the lithium oxalate. It is believed that during the reaction, there is a dissolution of the gibbsite followed by a re-precipitation of the new compound. Consideration is also given to the fact that an intercalation type reaction occurs between the lithium oxalate and the hydroxyl groups located between the layers of aluminum in the gibbsite.

Figure 2:
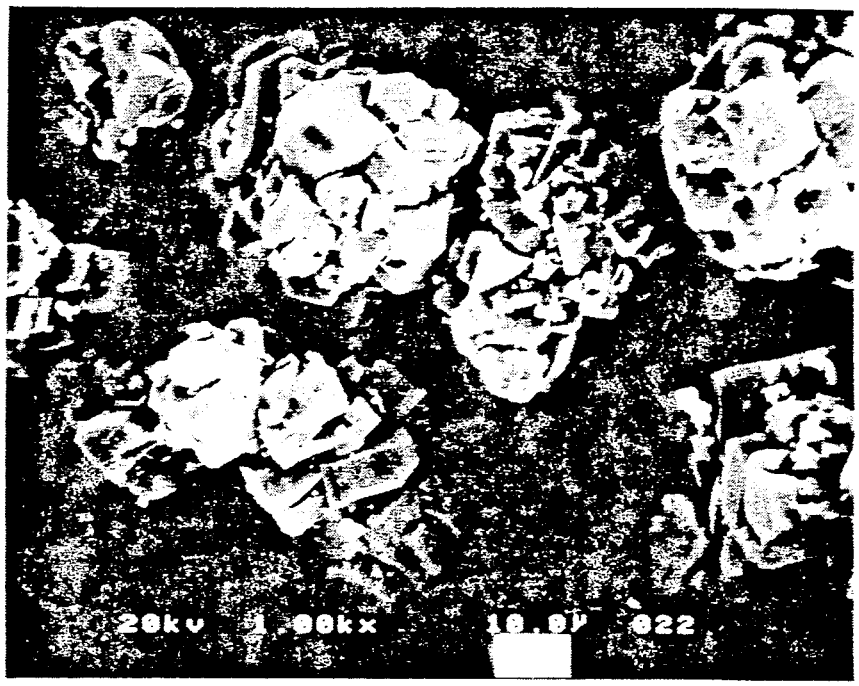
FIG. 2 is a micrograph showing particles of gibbsite.
Figure 3:
FIG. 3 is a micrograph showing expanded particles of the new compound resulting from gibbsite and lithium oxalate.

From an examination of FIG. 2, it will be seen that aluminum hydroxide particles (original gibbsite) are shown as solids. However, these particles, after reaction, are shown as greatly expanded particles which only generally depict the outline of the particles formed from platelets, needles, joined at the center (see FIG. 3). The particles of the new compound may have the general outline of the original particle but be composed of differently interwoven threads, strips, plates and rods.

The X-ray diffraction patterns show the presence of the original compound, e.g., gibbsite, as well as new lines specific to the lithium oxalate used (see FIG. 1). However, these new lines do not correspond to the lithium oxalate used or to the aluminum salt of the lithium oxalate where such a salt is known to exist. For example, the X-ray diffraction pattern of aluminum oxalate is reported in the Powder Diffraction File (JCPDS) published by International Centre for Diffraction Date, Swarthmore, PA 19081.

EXAMPLE 45 g (0.441 mols) of lithium oxalate (Li$_2$C$_2$O$_4$) was dissolved in 400 mls of water (1.1 molar solution). 20 g of crystalline Al(OH)$_3$ (gibbsite) (0.256 mols) was added to the solution and the mixture heated in a well-agitated closed reaction vessel to 175° C. under autogenous pressure for a period of 4 hours. The reactor was then cooled and the product filtered, washed thoroughly with hot water and dried overnight at 105° C. The weight of the product was 32.7 g. FIG. 1 is an X-ray diffraction pattern of this product. The chemical composition of the product was analyzed to be:

| Component | Actual wt. % | Wt. % Calculated Using the Formula Al$_2$(OH)$_6$·Li$_2$C$_2$O$_4$ |
|---|---|---|
| Al | 21.0 | 20.9 |
| Li | 4.8 | 5.4 |
| C | 8.8 | 9.3 |
| H$_2$O | 17.7 | 20.9 |
| Loss on ignition to 1200° C. | 50.0 | 55.0 |

The nearest chemical formula of the compound calculated from this chemical composition is Al$_2$(OH)$_6$·Li$_2$C$_2$O$_4$. FIG. 1, which shows the X-ray diffraction pattern of this new compound, is compared with the X-ray diffraction of the starting gibbsite and lithium oxalate. The X-ray diffraction of the new compound shows new lines which characterize this compound. These lines are in addition to the X-ray diffraction lines of the original gibbsite. However, it will be appreciated that the lithium oxalate X-ray diffraction lines are not present in the compound. The same behavior is confirmed by NMR and IR results. The SEM picture shows the morphology of the new compound formed (see FIG. 3). This may be compared with the SEM picture of the starting gibbsite. Chemical analysis of the new compound shows that 0.405 moles of lithium oxalate had reacted with each mole of gibbsite. The X-ray diffraction of the new compound and the crystal morphology show that a new compound has been formed under the above reaction conditions.

Having thus described the invention, what is claimed is:

1. A method of preparing crystalline compounds having a chemical composition expressed, in terms of molar ratios, by the formula:

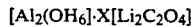

wherein X is equal to or less than 1, the method comprising the steps of:
 (a) dissolving a lithium oxalate in water to provide a solution having an lithium oxalate concentration in the range of 0.01 to 3.0 moles;
 (b) adding aluminum hydroxide to said solution to provide a concentration thereof in the range of 0.1 to 3.0 moles per mole of lithium oxalate;
 (c) heating said mixture to a temperature in the range of 100° to 250° C. to cause said oxalate to react with said aluminum hydroxide to form said crystalline compound; and
 (d) recovering the compound from the solution.

2. A method of making a new crystalline product having the composition, expressed in terms of molar ratios, by the formula [Al$_2$(OH)$_6$]·X[Li$_2$C$_2$O$_4$] where X is 1 or less than 1 and greater than zero, the method comprising reacting a mixture of an aluminum hydroxide material and a lithium oxalate to form said crystalline compound.

3. The method in accordance with claim 2 wherein aluminum hydroxide is gibbsite.

4. The method in accordance with claim 2 wherein aluminum hydroxide is bayerite.

5. The method in accordance with claim 2 wherein aluminum hydroxide is nordstrandite.

6. The method in accordance with claim 2 wherein aluminum hydroxide is boehmite.

7. The method in accordance with claim 2 wherein prior to reacting, said lithium oxalate is dissolved in a liquid.

8. The method in accordance with claim 7 wherein after dissolving, the lithium oxalate is mixed with the aluminum hydroxide.

9. The method in accordance with claim 2 wherein the mixture is heated for said reaction.

10. The method in accordance with claim 2 wherein the mixture is heated at a temperature of at least 100° C. for a time of at least 20 minutes.

11. The method in accordance with claim 2 wherein after said reacting, the compound is filtered, washed and dried.

12. A method of preparing crystalline compounds having a chemical composition expressed, in terms of molar ratios, by the formula:

$$[Al_2(OH)_6] \cdot X[Li_2C_2O_4]$$

where X is in the range of about 0.1 to 1, the method comprising the steps of:
(a) dissolving a lithium oxalate in a liquid solvent to provide a solution;
(b) adding aluminum hydroxide to said solution to form a mixture;
(c) heating said mixture to a temperature sufficient to cause said lithium oxalate to react with said aluminum hydroxide to form said compound; and
(d) recovering said compound.

13. The method in accordance with claim 11 wherein the solvent is selected from water and alcohol.

14. The method in accordance with claim 12 wherein the aluminum hydroxide in $Al(OH)_3$.

15. The method in accordance with claim 12 wherein the aluminum hydroxide is $AlO(OH)$.

16. The method in accordance with claim 12 wherein the reaction is carried out between 100° and 300° C.

* * * * *